US009487838B2

(12) United States Patent
Van De Sand et al.

(10) Patent No.: US 9,487,838 B2
(45) Date of Patent: Nov. 8, 2016

(54) OLIGONUCLEOTIDE PROBE FOR THE DETECTION OF ADENOVIRUS

(75) Inventors: Claudia Van De Sand, Hamburg (DE); Melanie Janssen-Weets, Bremen (DE); Nele Königsfeld, Hamburg (DE)

(73) Assignee: QIAGEN HAMBURG GMBH, Hilden (DE)

( * ) Notice: Subject to any disclaimer, the term of this patent is extended or adjusted under 35 U.S.C. 154(b) by 333 days.

(21) Appl. No.: 13/977,411

(22) PCT Filed: Dec. 28, 2010

(86) PCT No.: PCT/EP2010/070785
§ 371 (c)(1),
(2), (4) Date: Jul. 31, 2013

(87) PCT Pub. No.: WO2012/089240
PCT Pub. Date: Jul. 5, 2012

(65) Prior Publication Data
US 2014/0106335 A1    Apr. 17, 2014

(51) Int. Cl.
*C12P 19/34* (2006.01)
*C12Q 1/70* (2006.01)

(52) U.S. Cl.
CPC ........... *C12Q 1/701* (2013.01); *C12Q 2600/16* (2013.01)

(58) Field of Classification Search
CPC .......................... C12Q 1/701; C12Q 2600/16
USPC ................................................. 435/91.2, 6.1
See application file for complete search history.

(56) References Cited

U.S. PATENT DOCUMENTS

| | | | |
|---|---|---|---|
| 5,210,015 | A | 5/1993 | Gelfand et al. |
| 5,925,517 | A | 7/1999 | Tyagi et al. |
| 6,326,145 | B1 | 12/2001 | Whitcombe et al. |
| 7,235,358 | B2 | 6/2007 | Wohlgemuth et al. |
| 2006/0240412 | A1* | 10/2006 | Hall ....................... C12Q 1/701 435/5 |

FOREIGN PATENT DOCUMENTS

WO       2006024892       3/2006

OTHER PUBLICATIONS

Johnson et al., Clinical Virology Laboratory Testing, Abstract D-2255—Wolke, Oct. 2008.*
Leruez-Ville et al., "Real-time blood plasma polymerase chain reaction for management of disseminated adenovirus infection," Clin. Infect. Dis., 2004, vol. 38, No. 1, 45-52, abstract only attached.
Gu et al., "Multiplexed, real-time PCR for quantitative detection of human adenovirus," J. Clin. Microbiol., 2003, ol. 41, No. 10, 4636-41, abstract only attached.

Osiowy, "Direct detection of respiratory syncytial virus, parainfluenza virus, and adenovirus in clinical respiratory specimens by a multiplex reverse transcription-PCR assay," J. Clin. Microbiol., 1998, vol. 36, No. 11, 3149-54, abstract only attached.
International Search Report dated May 20, 2011 in corresponding PCT/EP2010/070785 filed on Dec. 28, 2010.
International Preliminary Report on Patentability dated Apr. 30, 2013 in corresponding PCT/EP2010/070785 filed on Dec. 28, 2010.
Leruez-Ville et al., "Real-Time Blood Plasma Polymerase Chain Reaction for Management of Disseminated Adenovirus Infection," Clinical Infectious Diseases, The University of Chicago Press, Chicago, IL, 2004, vol. 38, No. 1, 45-52 (8 pages).
Gu Z et al: "Multiplexed, real-time PCR for quantitative detection of human adenovirus", Journal of Clinical Microbiology, American Society for Microbiology, Washington, DC, US, vol. 41, No. 10, Oct. 1, 2003 (Oct. 1, 2003), pp. 4636-4641 (6 pages).
Chapter 10: "Working with synthetic oligonucleotide probes" In: Sambrook & Russell, Molecular Cloning, A Laboratory Manual, Cold Spring Harbor Laboratory Press, Cold Spring Harbor, N.Y., 3rd edition (2001) (55 pages).
Nazarenko et al.: "A closed tube format for amplification and detection of DNA based on energy transfer" Nucleic Acids Research 25:2516-21, 1997 (6 pages).
Chen et al.: "An Automated Fluorescent PCR Method for Detection of Shiga Toxin-Producing Escherichia coli in Foods" Applied and Environmental Microbiology 64:4210-6, 1998 (7 pages).
Lay & Wittwer: "Real-time fluorescence genotyping of factor V Leiden during rapid-cycle PCR" Clinical Chemistry 43:2262-2267, 1997 (6 pages).
Li et al: "A new class of homogeneous nucleic acid probes based on specific displacement hybridization" Nucleic Acids Research 30:E5, 2002 (9 pages).
Howell et al..: "iFRET: An Improved Fluorescence System for DNA-Melting Analysis" Genome Research 12:1401-1407, 2002 (8 pages).
Marras et al: "Real-time assays with molecular beacons and other fluorescent nucleic acid hybridization probes", European Journal of Internal Medicine, Clinica Chimica Acta, 363:48-60, 2006 (13 pages).
ResPlex II Panel v2.0 Handbook, Qiagen, Sample & Assay Technologies, Sep. 2010 (28 pages).
Database EMBL [Online] Aug. 14, 2007, "Sequence 8016 from patent U.S. Pat. No. 7235358.", XP002637311, retrieved from EBI accession No. EM_PAT:EA260090 Database accession No. EA260090 (1 page).
Database EMBL [Online] May 26, 2009, "Sequence 63173 from Patent WO2006024892.", XP002637312, retrieved from EBI accession No. EM_PAT:HA251242 Database accession No. HA251242 (1 page).
Database EMBL [Online] Nov. 1, 1997, "Homo sapiens chromosome 8 STS.", XP002637313, retrieved from EBI accession No. EMBL:U92553 Database accession No. U92553 (1 page).

(Continued)

*Primary Examiner* — Cynthia B Wilder
(74) *Attorney, Agent, or Firm* — Hovey Williams LLP

(57) ABSTRACT

The present invention relates to an oligonucleotide probe for the detection of adenoviral nucleic acid in a biological sample. In a further aspect, the invention relates to a method for the detection of an adenoviral nucleic acid in a biological sample. The invention also provides oligonucleotide primers for amplifying adenoviral nucleic acid. Kits comprising probes and/or primers of the invention are also provided. Finally, the invention also relates to the use of the oligonucleotide primers and/or probes for detecting adenoviral nucleic acid.

15 Claims, 1 Drawing Sheet

(56) References Cited

OTHER PUBLICATIONS

Osiowy: "Direct detection of respiratory syncytial virus, parainfluenza virus, and adenovirus in clinical respiratory specimens by a multiplex reverse transcription-PCR assay.", Journal of Clinical Microbiology, vol. 36, No. 11, Nov. 1, 1998, pp. 3149-54 (6 pages).

"Database entry AB366015, partial coding sequence of Norovirus", Oct. 30, 2007, XP055052300, [retrieved on Feb. 5, 2013](Al-Mashhadani et al.: Norovirus Gastroenteritis among Children in Iraqi Kurdistan, unpublished) (1 page).

Database entry DQ182107, Norovirus causing traveler's diarrhea, Jan. 1, 2005, XP055052314, [retrieved on Feb. 5, 2013](Ko et al.: Noroviruses as a Cause of Traveler's Diarrhea among Students from the United States Visiting Mexico.—J. Clin. Microbiol., 43 Dec. 2005, p. 6126-6129) (5 pages).

Written Opinion of the International Preliminary Examining Authority dated Nov. 29, 2012 in corresponding PCT/EP2010/070785 filed on Dec. 28, 2010 (9 pages).

Written Opinion of the International Preliminary Examining Authority dated Mar. 12, 2013 in corresponding PCT/EP2010/070785 filed on Dec. 28, 2010 (10 pages).

* cited by examiner

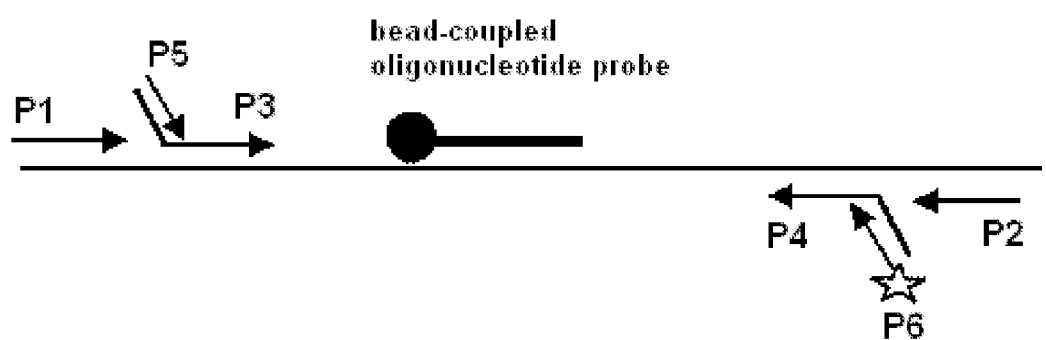

SEQUENCE LISTING

<160> NUMBER OF SEQ ID NOS: 17

<210> SEQ ID NO 1
<211> LENGTH: 17
<212> TYPE: DNA
<213> ORGANISM: Artificial
<220> FEATURE:
<223> OTHER INFORMATION: Oligonucleotide probe

<400> SEQUENCE: 1
attattgaaa accatgg                          17

<210> SEQ ID NO 2
<211> LENGTH: 21
<212> TYPE: DNA
<213> ORGANISM: Artificial
<220> FEATURE:
<223> OTHER INFORMATION: Oligonucleotide probe

<400> SEQUENCE: 2
cgcattattg aaaaccatgg c                     21

<210> SEQ ID NO 3
<211> LENGTH: 17
<212> TYPE: DNA
<213> ORGANISM: Artificial
<220> FEATURE:
<223> OTHER INFORMATION: Oligonucleotide primer

<400> SEQUENCE: 3
caggacagaa acactga                          17

<210> SEQ ID NO 4
<211> LENGTH: 21
<212> TYPE: DNA
<213> ORGANISM: Artificial
<220> FEATURE:
<223> OTHER INFORMATION: Oligonucleotide primer

<400> SEQUENCE: 4
ttggatattg atttccatag c                     21

<210> SEQ ID NO 5
<211> LENGTH: 19
<212> TYPE: DNA
<213> ORGANISM: Artificial
<220> FEATURE:
<223> OTHER INFORMATION: Oligonucleotide primer

<400> SEQUENCE: 5
gattaatttc cagggcaaa                        19

<210> SEQ ID NO 6
<211> LENGTH: 16
<212> TYPE: DNA
<213> ORGANISM: Artificial
<220> FEATURE:
<223> OTHER INFORMATION: Oligonucleotide primer

<400> SEQUENCE: 6
ctatgtggaa tcaggc                           16

<210> SEQ ID NO 7
<211> LENGTH: 18
<212> TYPE: DNA
<213> ORGANISM: Artificial
<220> FEATURE:
<223> OTHER INFORMATION: Oligonucleotide primer
<220> FEATURE:
<221> NAME/KEY: modified_base
<222> LOCATION: (12)..(12)
<223> OTHER INFORMATION: I

<400> SEQUENCE: 7
gatcctgatg tncgcatt                         18

-continued

```
<210> SEQ ID NO 8
<211> LENGTH: 16
<212> TYPE: DNA
<213> ORGANISM: Artificial
<220> FEATURE:
<223> OTHER INFORMATION: Oligonucleotide primer

<400> SEQUENCE: 8
cagttccatg gttttc                                                       16

<210> SEQ ID NO 9
<211> LENGTH: 15
<212> TYPE: DNA
<213> ORGANISM: Artificial
<220> FEATURE:
<223> OTHER INFORMATION: Oligonucleotide primer

<400> SEQUENCE: 9
cacgccatga ttttc                                                        15

<210> SEQ ID NO 10
<211> LENGTH: 19
<212> TYPE: DNA
<213> ORGANISM: Artificial
<220> FEATURE:
<223> OTHER INFORMATION: Oligonucleotide primer

<400> SEQUENCE: 10
tttctatgtg gaatcaggc                                                    19

<210> SEQ ID NO 11
<211> LENGTH: 21
<212> TYPE: DNA
<213> ORGANISM: Artificial
<220> FEATURE:
<223> OTHER INFORMATION: Oligonucleotide primer
<220> FEATURE:
<221> NAME/KEY: modified_base
<222> LOCATION: (15)..(15)
<223> OTHER INFORMATION: I

<400> SEQUENCE: 11
tatgatcctg atgtncgcat t                                                 21

<210> SEQ ID NO 12
<211> LENGTH: 19
<212> TYPE: DNA
<213> ORGANISM: Artificial
<220> FEATURE:
<223> OTHER INFORMATION: Oligonucleotide primer

<400> SEQUENCE: 12
cagttccatg gttttcaat                                                    19

<210> SEQ ID NO 13
<211> LENGTH: 18
<212> TYPE: DNA
<213> ORGANISM: Artificial
<220> FEATURE:
<223> OTHER INFORMATION: Oligonucleotide primer

<400> SEQUENCE: 13
cacgccatga ttttcaat                                                     18

<210> SEQ ID NO 14
<211> LENGTH: 39
<212> TYPE: DNA
```

```
<213> ORGANISM: Artificial
<220> FEATURE:
<223> OTHER INFORMATION: Oligonucleotide primer

<400> SEQUENCE: 14
caggccacgt tttgtcatgc tttctatgtg gaatcaggc                              39

<210> SEQ ID NO 15
<211> LENGTH: 41
<212> TYPE: DNA
<213> ORGANISM: Artificial
<220> FEATURE:
<223> OTHER INFORMATION: Oligonucleotide primer
<220> FEATURE:
<221> NAME/KEY: modified_base
<222> LOCATION: (35)..(35)
<223> OTHER INFORMATION: I

<400> SEQUENCE: 15
caggccacgt tttgtcatgc tatgatcctg atgtncgcat t                           41

<210> SEQ ID NO 16
<211> LENGTH: 39
<212> TYPE: DNA
<213> ORGANISM: Artificial
<220> FEATURE:
<223> OTHER INFORMATION: Oligonucleotide primer

<400> SEQUENCE: 16
ttctttgcgt tatgtctctg cagttccatg gttttcaat                              39

<210> SEQ ID NO 17
<211> LENGTH: 38
<212> TYPE: DNA
<213> ORGANISM: Artificial
<220> FEATURE:
<223> OTHER INFORMATION: Oligonucleotide primer

<400> SEQUENCE: 17
ttctttgcgt tatgtctctg cacgccatga ttttcaat                               38
```

OLIGONUCLEOTIDE PROBE FOR THE DETECTION OF ADENOVIRUS

RELATED APPLICATIONS

This application is the National Stage of International Patent Application No. PCT/EP2010/070785, filed Dec. 28, 2010, which is hereby incorporated by reference in its entirety.

SEQUENCE LISTING

The sequences listed in the accompanying Sequence Listing are presented in accordance with 37 C.F.R. 1.822. The Sequence Listing is submitted as an ASCII computer readable text file, which is incorporated by reference herein.

FIELD OF THE INVENTION

The present invention relates to an oligonucleotide probe for the detection of adenoviral nucleic acid in a biological sample. In a further aspect, the invention relates to a method for the detection of an adenoviral nucleic acid in a biological sample. The invention also provides oligonucleotide primers for amplifying adenoviral nucleic acid. Kits comprising probes and/or primers of the invention are also provided. Finally, the invention also relates to the use of the oligonucleotide primers and probes for amplifying or detecting adenoviral nucleic acid.

TECHNICAL BACKGROUND

Human adenoviruses have long been recognized as pathogens, causing a broad spectrum of diseases. Most commonly, adenoviruses cause respiratory diseases. Depending on the infecting serotype, they may also cause various other diseases, such as gastroenteritis, conjunctivitis, rash and cystitis. Symptoms of respiratory illness caused by adenovirus infection include the common cold syndrome, pneumonia, croup and bronchitis. Patients with compromised immune systems are especially susceptible to severe complications of adenovirus infection. Acute respiratory disease (ARD) can be caused by adenovirus infections during conditions of crowding and stress.

Since a high number of viral and bacterial pathogens can cause similar symptoms, accurate identification of the etiologic agent is very important for specific classification and differentiation as well as for subsequent treatment.

Adenoviruses are medium-sized (90-100 nm), non-enveloped icosohedral viruses containing double-stranded DNA. There are 49 immunologically distinct serotypes which are classified in 6 different subtypes (A through F) that can cause human infections.

Although epidemiologic characteristics of the adenoviruses vary by type, all are transmitted by direct contact, faecaloral transmission, and occasionally waterborne transmission. Some adenoviruses (e.g. serotypes 1, 2, 5, and 6) have been shown to be endemic in parts of the world where they have been studied, and infection is usually acquired during childhood.

Acute respiratory disease is most often associated with adenovirus types 4 and 7 in the United States. For some adenovirus serotypes, the clinical spectrum of disease associated with infection varies depending on the site of infection; for example, infection with adenovirus 7 acquired by inhalation is associated with severe lower respiratory tract disease, whereas oral transmission of the virus typically causes no or mild disease. Outbreaks of adenovirus-associated respiratory disease have been common in the late winter, spring, and early summer.

Several methods have been established for the identification of adenovirus infections. While conventional methods such as visualization by electron microscopy, viral culture or agglutination assays with antibody-coated beads are tedious and time-consuming, other methods such as dot blot hybridization lack a sufficiently high sensitivity and are not amenable to high-throughput. Therefore, detection assays have been developed which are based on polymerase chain reaction (PCR). For example, real-time PCR methods for detecting and quantifying the adenoviral load in immunosuppressed patients have been established (Leurez-Ville et al. 2004, *Clin. Infect. Dis.*, 38: 45-52). Multiplex real-time PCR methods for the detection of adenoviruses have also been described (Gu et al., 2003, *J. Clin. Microbiol.* 41: 4636-4641). One problem encountered in the detection of adenoviruses via PCR resides in the high sequence diversity between different adenovirus subtypes and serotypes which results in a high degree of mismatching of viral DNA with primers and probes which are aimed at the detection of all subtypes in a biological sample. As a consequence, sensitivity and specificity of the PCR methods described in the prior art is low.

The problem underlying the present invention is the provision of primers and probes that allow for the reliable detection of essentially all adenovirus serotypes in a sample which are involved in respiratory infections, in particular serotypes 1, 2, 3, 4, 5, 6, 7, 11, 14, 16, 21, 34, and 35. Theses adenovirus serotypes belong to the subtypes B, C and E. The primers and probes should in particular be suitable for use in a multiplex PCR approach for the parallel detection of different viral and/or bacterial pathogens.

SUMMARY OF THE INVENTION

The present invention provides means and methods for detecting nucleic acid from adenovirus serotypes which cause respiratory diseases in humans. In a first aspect, the present invention provides an oligonucleotide probe which comprises or consists of one of the following sequences:
 a) the nucleotide sequence of SEQ ID NO:1; or
 b) a sequence which is at least 85% identical to the nucleotide sequence of SEQ ID NO:1;
 c) the complement of (a) or (b).

It has been found that a hybridization probe which comprises or consists of the nucleotide sequence depicted in SEQ ID NO:1 can be used for the reliable and reproducible detection of DNA or RNA derived from the hexon gene of all adenovirus serotypes which have been found to be involved in respiratory infections in humans (serotypes from adenovirus subtypes B, C and E). It has been shown in the course of the invention that an oligonucleotide probe comprising the nucleotide sequence of SEQ ID NO:1 specifically hybridizes to DNA or RNA of all adenovirus serotypes which are associated with respiratory diseases in humans. A probe having the nucleotide sequence of SEQ ID NO:1 can therefore be used as a universal probe in a diagnostic assay for the detection of respiratory diseases caused by adenoviruses.

In a preferred embodiment of the invention, the hybridization probe comprises or consists of:
 a) the nucleotide sequence of SEQ ID NO:2; or
 b) a sequence which is at least 85% identical to the nucleotide sequence of SEQ ID NO:2;
 c) the complement of (a) or (b).

The probe depicted in SEQ ID NO:2 differs from the nucleotide sequence of SEQ ID NO:1 in that it comprises 3 additional nucleotides at the 5' end and one additional nucleotide at the 3' end of the oligonucleotide. The hybridization probe of SEQ ID NO:2 therefore has a higher affinity for the adenoviral target DNA or RNA, i.e. the adenoviral hexon gene, and can thus be used under more stringent hybridization conditions compared to the probe of SEQ ID NO:1.

The invention also contemplates the use of probe molecules comprising or consisting of sequences which are complementary to the sequence of SEQ ID NO:1 or SEQ ID NO:2.

As will be understood by those skilled in the art, a limited degree of sequence variation relative to the nucleotide sequence of SEQ ID NO:1 or SEQ ID NO:2 or their complements may occur without affecting the functional reliability of the oligonucleotide probe. For example, sequence variants may be used having one or more (e.g. 1, 2, 3) substitutions, insertions or deletions of nucleotides relative to the sequence of SEQ ID NO:1 or SEQ ID NO:2 or their complements. The variant will have at least 85% sequence identity to the sequence of SEQ ID NO:1 or SEQ ID NO:2 or their complements, preferably at least 86, 87, 88, 89, 90, 91, 92, 93, 94, or 95% sequence identity. In a particularly preferred aspect of the invention, the oligonucleotide probe consists of the sequence of SEQ ID NO:1 or SEQ ID NO:2.

As used herein in connection with probes and primer molecules, the term oligonucleotide denotes a molecule consisting of at least 5 nucleotides, preferably at least 10, 15, 20, 25, 30 or 35 nucleotides. The length of the molecule will be up to 35 nucleotides, preferably up to 40, 45, 50, 55, or 60 nucleotides. In other words, an oligonucleotide as defined herein will have a length of 5-60, more preferably 10-50, 15-40, 20-35 or 25-35 nucleotides.

Apart from oligonucleotide probes, the present invention also provides oligonucleotide primers which are particularly suited for use in amplifying nucleic acid (such as DNA) of adenoviruses that are associated with respiratory diseases in humans. The primers set forth by the present invention are depicted in SEQ ID NOs:3-13. These primers bind in the region of the adenoviral hexon gene of all adenovirus serotypes that may act as a causative agent for respiratory diseases. Specifically, the primers bind to DNA of adenovirus serotypes 1, 2, 3, 4, 5, 6, 7, 11, 14, 16, 21, 34, and 35 and can thus be used in the diagnosis of adenovirus-mediated respiratory disease or disorder. More specifically, the primer of SEQ ID NO:3 binds to each of the above adenovirus serotypes, while the corresponding reverse primer depicted in SEQ ID NO:4 binds to serotypes 3, 4, 7, 14, 34 and 35. The alternative reverse primer of SEQ ID NO:5 binds to serotypes 1, 2, 5, 6, 11, 16 and 21. The primers of SEQ ID NO:6 und SEQ ID NO:10 specifically bind to serotypes 1, 2, 5, 6, 14, and the primers of SEQ ID NO:7 und SEQ ID NO:11 bind to 3, 4, 7, 11, 16, 21, 34, 35. Primers as depicted in SEQ ID NO:8 und SEQ ID NO:12 bind to serotypes 3, 4, 7, 11, 14, 16, 21, 34, 35. The primers depicted in SEQ ID NO:9 and SEQ ID NO:13 are capable of binding to serotypes 1, 2, 5, and 6.

In one aspect, the present invention therefore relates to an oligonucleotide primer comprising:
a) the nucleotide sequence of any of SEQ ID NOs:3-9; or
b) a sequence which is at least 85% identical to a nucleotide sequence of any of SEQ ID NOs:3-9; or
c) the complement of (a) or (b).

In an even more preferred aspect, the invention relates to oligonucleotide primers comprising:
a) the nucleotide sequence of any of SEQ ID NOs:3-5 and 10-13; or
b) a sequence which is at least 85% identical to a nucleotide sequence of any of SEQ ID NOs:3-5 and 10-13; or
c) the complement of (a) or (b).

The primers set forth in SEQ ID NOs:6-7 differ from those in SEQ ID NOs:10-11 in that the latter include 3 additional nucleotides at their 5' end of the oligonucleotide molecule. Similarly, the oligonucleotide primers depicted in SEQ ID NOs:8-9 differ from those in SEQ ID NOs:12-13 in that the latter comprise 3 additional nucleotides at their 3' end. Owing to the additional terminal nucleotides, an enhanced base pairing with the adenoviral target sequence is achieved with the longer primer molecules. Accordingly, the primers of SEQ ID NOs:10-13 may be used under more stringed hybridization conditions than those having a sequence of SEQ ID NOs:6-9. In a preferred embodiment the oligonucleotide primer of the invention consist of one of the nucleotide sequences of SEQ ID NOs:3-13.

The primers depicted in SEQ ID NOs:3, 6, 7, 10 and 11 are forward primers which can be combined with corresponding reverse primers so as to form a primer pair that can be used for the amplification of the adenoviral hexon gene sequence of serotypes associated with respiratory diseases. Preferably, the primer of SEQ ID NO:3 is used in combination with the primer of SEQ ID NOs:4 and/or 5. These primer pairs (SEQ ID NO:3/SEQ ID NO:4 and SEQ ID NO:3/SEQ ID NO:5) can be used to amplify a larger fragment of the adenoviral hexon gene. In a subsequent step, the amplified fragment itself serves as a template for amplification with a second primer pair ("nested PCR").

In the present case, the second primer pair which uses the amplification product of the first primer pair as a template consists of the primer shown in SEQ ID NO:6 (or the longer variant of SEQ ID NO:10) and the primer of SEQ ID NO:9 (or the longer variant of SEQ ID NO:13). It will of course readily be possible to combine one of the longer primer variants depicted with the short version of its corresponding primer. Thus, the combinations SEQ ID NOs:10 and 13, SEQ ID NOs:10 and 9, SEQ ID NOs:6 and 9, SEQ ID NOs:6 and 13 may be used as a second primer pair.

An alternative second primer pair consists of the primer of SEQ ID NO:7 (or the longer variant of SEQ ID NO:11) and the primer of SEQ ID NO:8 (or the longer variant of SEQ ID NO:12). As indicated above, it is readily possible to combine longer and shorter versions of the different primers (i.e. one may use the primer pairs SEQ ID NOs:11 and 8, SEQ ID NOs:11 and 12, SEQ ID NOs:7 and 8, SEQ ID NOs:7 and 12) as a second primer pair. These primers are capable of detecting other adenovirus serotypes than the primers shown in SEQ ID NOs:6, 8, and 12. Therefore, it is particularly preferable to use both second primer pairs in parallel in a multiplex PCR assay to cover a high number of different adenovirus serotypes in a single assay (see examples below).

As already described in the context with the oligonucleotide probes of SEQ ID NO:1 or SEQ ID NO:2, the invention also contemplates the use of primers which comprise a nucleotide sequence that is essentially identical to one of SEQ ID NOs:3-13, but differs from the reference sequence by one or more (e.g. 1, 2, 3) substitutions, insertions or deletions of nucleotides. Such sequence variations are acceptable as long as they do not affect the reliability of the oligonucleotide primers in the amplification of the adenovirus DNA. The variant will have at least 85% sequence identity to a sequence of SEQ ID NOs:3-13 or their complements, preferably at least 86, 87, 88, 89, 90, 91, 92, 93, 94, or 95% sequence identity.

The oligonucleotide probes and primers may be used in different methods which include the specific hybridization of the oligonucleotide primers and probes of the invention to adenoviral target nucleic acid. In its broadest sense, the present invention provides a method for detecting an adenovirus nucleic acid in a biological sample, comprising a) obtaining viral nucleic acid from a biological sample;
b) amplifying the viral nucleic acid;
c) contacting the oligonucleotide probe as defined above with the amplified viral nucleic acid obtained in step b);
d) detecting specific hybridization of the oligonucleotide probe to the amplified viral nucleic acid;

wherein the specific hybridization indicates that the sample contains adenovirus nucleic acid.

Preferably, the viral nucleic acid is DNA or RNA from adenovirus subtypes B, C or E. More preferably, it is from one of the adenovirus serotypes which are involved in respiratory infections, preferably serotypes 1, 2, 3, 4, 5, 6, 7, 11, 14, 16, 21, 34, and 35. In a particularly preferred embodiment, the adenovirus nucleic acid to be detected is adenovirus DNA from an adenoviral hexon gene.

In the first step of the method of the invention, viral nucleic acid is obtained from a biological sample. The biological sample refers to any kind of sample which is suspected to include adenoviral material. In particular, the biological sample is a clinical sample, e.g. a tissue or fluid sample which has been isolated from a subject, preferably a human subject. Clinical samples include, for example, biopsies, in particular aspirate biopsies, blood serum, plasma, urine, stool, sputum, bronchial lavage, liquor, and nasal or throat swabs. Preferably, the biological sample is from a human subject. Any viral nucleic acid that may be present in the sample is separated from the sample material by means of commonly available kits for the purification of viral DNA or RNA (e.g. the QIAamp MiniElute Virus Spin Kit, Qiagen, Hilden, Germany).

In the next step, the viral nucleic acid extracted from the sample is amplified before being contacted with the hybridization probe. In this manner the amount of the adenoviral target nucleic acid is increased prior to contact with the oligonucleotide probe of the invention. Where the nucleic acid extracted from the biological sample is viral DNA, the amplification can be achieved by a polymerase chain reaction. A polymerase chain reaction is an enzymatic reaction for increasing the amount or concentration of a DNA sequence which is catalyzed by a thermostable DNA-dependent DNA polymerase. The primers are complementary to one strand of the double-stranded target sequence. For amplification, the double-stranded target sequence is denatured so as to allow annealing of the primers. Following annealing, the primers are extended by means of the DNA polymerase to form a new pair of complementary strands. The steps of denaturation, primer annealing, and polymerase extension are repeated several times, e.g. 15-35 times, to obtain a high amount or concentration of the target DNA sequence. PCR amplification methods are well-known to the skilled person, and PCR kits are purchasable from many different manufacturers. The oligonucleotide primers and probes defined above can be used for the amplification and detection of adenoviral DNA from the hexon gene.

Alternatively, the oligonucleotide probes and primers of the present invention may also be used in an RT-PCR reaction. Where the nucleic acid extracted from the biological sample is RNA (e.g. total RNA or mRNA), the first step of the amplification is a reverse transcription reaction (RT). In this reaction, the adenoviral RNA is transcribed into cDNA by means of a reverse transcriptase enzyme. Suitable enzymes are known to the skilled person and include the M-MLV reverse transcriptase from the Moloney murine leukemia virus and the AMV reverse transcriptase from the avian myeloblastosis virus. Reverse transcription can be achieved by use of a sequence specific primer or an oligo-d(T) primer which is complementary to the poly (A) tail of the RNA. The cDNA generated by the reverse transcriptase is then used as a template in a subsequent PCR reaction. An amplification reaction comprising a reverse transcription reaction and a subsequent PCR amplification reaction is referred to as "RT-PCR" herein. According to the present invention, the RT-PCR can be performed as a one-step or two-step RT-PCR. The primers and probes defined above can be used for specifically amplifying and detecting adenoviral nucleic acid when starting from a RNA preparation that was derived from the biological sample.

For detection of the amplified adenoviral DNA, the oligonucleotide probe according to the invention is contacted with the amplified adenoviral nucleic acid. For example, the probe can be used in a conventional Southern blot assay where the probe is hybridized to adenovirus DNA isolated from the biological sample. In an alternative embodiment, the probe may be used in a Northern blot assay to detect adenoviral RNA (total RNA or mRNA) derived from the biological sample. When used for Southern or Northern blotting, the oligonucleotide probes of the invention will be linked with a suitable label to generate a detectable signal after hybridization to the target DNA or RNA. Suitable labels include radioisotopes, such as $^{32}$P and $^{35}$S; chromophores; fluorophores, such as rhodamine, phycoerythrin, fluorescein, Cy3 and Cy5; heavy metals, such as gold; antibodies; electron dense particles; enzymes, such as alkaline phosphatase and horseradish peroxidase; cofactors; substrates for enzymes; and the like. The oligonucleotide probe may also be linked to a bead, such as a colour-coded bead, which is detectable in a laser detection device.

Labelling is achieved by any of a number of methods known in the art, including random priming, nick translation, end labeling, chemical modification, and conjugation. Kits for the labeling of oligonucleotide probes are available from different manufacturers (e.g., the mirVana miRNA Probe Construction Kit, the BrightStar® Psoralen-Biotin non-isotopic Labeling Kit, and the DECAprime™ II Random Priming DNA Labeling Kit, all available from Applied Biosystems, Darmstadt, Germany; or the Amersham Alk-Phos Direct™ Labeling and Detection Systems, available from GE Healthcare Europe GmbH, Freiburg, Germany).

The probe is incubated with the viral nucleic acid under conditions which allow for the specific hybridization of the probe to its adenoviral target sequence. Suitable hybridization conditions can be determined by commonly known optimization procedures. Conditions such as hybridization temperature, salt concentration, pH, buffer components, and ionic strength may vary depending on the concrete length of the probe and other factors. More details regarding hybridization conditions can be found in Sambrook & Russell, Molecular Cloning, A Laboratory Manual, Cold Spring Harbor Laboratory Press, Cold Spring Harbor, N.Y., 3$^{rd}$ edition (2001).

Detection of specific hybridization of the oligonucleotide probe to the viral nucleic acid will depend on the nature of the label that was selected for labelling the probe. For example, if the oligonucleotide probe is labelled with a radioisotope, detection of the label will be achieved by autoradiography. Alternatively, where the probe is coupled to an alkaline phosphatase enzyme, the duplexes formed from the probe and the target sequence may be detected by use of a chemiluminescent substrate, such as AMPPD.

The probes and primers described herein are particularly suited for use in real-time PCR assays. In a real-time PCR method, it is possible to monitor the multiplication of the PCR products and quantify the amplified products in real time during amplification. The method is based on the principle that the detectable emission of fluorescence from fluorescent dyes is directly or indirectly associated with the formation of a newly-synthesized amplification product in each PCR cycle. Currently available real-time PCR methods can use different probes, such as TaqMan probes (U.S. Pat. No. 5,210,015), molecular beacons (U.S. Pat. No. 5,925,517), scorpions (U.S. Pat. No. 6,326,145), Amplifluor (Nazarenko et al., Nucleic Acids Res. 25:2516-21, 1997), Amplisensor (Chen et al., Appl. Environ. Microbiol. 64:4210-6, 1998), adjacent probes (Lay & Wittwer, Clin Chem. 43:2262-2267, 1997), double-stranded probes (Li et al., Nucleic Acids Res. 30:E5, 2002), iFRET probes (Howell et al., Genome Res 12:1401-1407, 2002), and the like. These probes are based on the "fluorescence resonance energy transfer" (FRET) technique and rely on the principle that a donor fluorophore absorbs excitation energy and delivers this energy to an acceptor fluorophore (also referred to as quencher) when the donor and acceptor molecules are sufficiently close to one another. When the donor fluorophore and acceptor fluorophore are separated in the amplification reaction, the increased distance between donor and acceptor fluorophore will result in increased fluorescence signal of the donor fluorophore and a decreased signal of the acceptor fluorophore owing to the decreased level of fluorescence resonance energy transfer.

The oligonucleotide probe of the present invention can be used for preparing one of the above-mentioned FRET probes for use in a real-time PCR method. The skilled person will readily be able to produce probes for use in real-time PCR method based on the nucleotide sequences referred to in SEQ ID NOs:1 and 2 and the extensive literature relating to real-time PCR available in the prior art. For example, when using the nucleotide sequences of SEQ ID NO:1 or 2 for preparing a double-labeled real-time PCR probe in the form of a molecular beacon, the skilled person will be aware that molecular beacon probes are single-stranded oligonucleotides having a stem-loop structure, which means that such probes form a hairpin structure in which a donor fluorophore and a acceptor fluorophore are attached to the opposite ends of the oligonucleotide. The skilled person will therefore add short complementary sequences to the probe sequence of SEQ ID NO:1 or 2 that allow the formation of an intramolecular stem, thereby bringing the donor and acceptor fluorophores into close proximity. The loop portion of the molecular beacon is complementary to the adenoviral target nucleic acid. When the molecular beacon harboring the sequence of SEQ ID NO:1 or 2 in the loop portion binds to the adenoviral target nucleic acid, the stem structure is destroyed and the donor and acceptor fluorophores move away from each other. Methods for the production of molecular beacons are described, for example, in Marras et al., Clin Chim Acta, 363:48-60, 2006.

In a further preferred embodiment, the probes and primers of the invention are used in a multiplex PCR method. As used herein, a multiplex PCR refers to a PCR reaction using multiple primer sets within a single PCR mixture to produce amplification products of varying sizes that are specific to different target sequences. A multiplex PCR can target a single gene or multiple genes. A common assay which is based on multiplex PCR is the simultaneous identification of several pathogenic bacteria or viruses from a clinical probe. An example for a multiplex PCR assay is the ResPlex II Panel v2.0 available from Qiagen (Hilden, Germany).

In a preferred aspect, a multiplex PCR is performed which uses as a first forward primer an oligonucleotide comprising: a) the nucleotide sequence of SEQ ID NO:6 or SEQ ID NO:10; or b) a sequence which is at least 85% identical to the nucleotide sequence of SEQ ID NO:6 or SEQ ID NO:10; or c) the complement of (a) or (b); and as a second forward primer an oligonucleotide comprising: a) the nucleotide sequence of SEQ ID NO:7 or SEQ ID NO:11; or b) a sequence which is at least 85% identical to a nucleotide sequence of SEQ ID NO:7 or SEQ ID NO:11; or c) the complement of (a) or (b); and as a first reverse primer an oligonucleotide comprising: a) the nucleotide sequence of SEQ ID NO:8 or SEQ ID NO:12; or b) a sequence which is at least 85% identical to a nucleotide sequence of SEQ ID NO:8 or SEQ ID NO:12; or c) the complement of (a) or (b); and as a second reverse primer an oligonucleotide comprising: a) the nucleotide sequence of SEQ ID NO:9 or SEQ ID NO:13; or b) a sequence which is at least 85% identical to a nucleotide sequence of SEQ ID NO:9 or SEQ ID NO:13; or c) the complement of (a) or (b). Such a multiplex design enables the parallel amplification of all relevant adenovirus serotypes which are associated with respiratory diseases.

In a particularly preferred embodiment, the multiplex PCR also uses an oligonucleotide comprising: a) the nucleotide sequence of SEQ ID NO:3; or b) a sequence which is at least 85% identical to the nucleotide sequence of SEQ ID NO:3; or c) the complement of (a) or (b) as a third forward primer; and an oligonucleotide comprising: a) the nucleotide sequence of SEQ ID NO:4 or SEQ ID NO:5; or b) a sequence which is at least 85% identical to the nucleotide sequence of SEQ ID NO:4 or SEQ ID NO:5; or c) the complement of (a) or (b) as a third reverse primer. By use of the primers of SEQ ID NOs:3-5, a larger segment of the hexon gene is amplified and is used as a template for a subsequent amplification reaction by the primers of SEQ ID NOs:6-9 (or SEQ ID NOs:10-13). By use of such nested PCR approach, the risk of unspecific amplification products can be significantly reduced.

In a particularly preferred embodiment, the multiplex PCR also uses an oligonucleotide probe comprising: a) the nucleotide sequence of SEQ ID NO:1 or 2; or b) a sequence which is at least 85% identical to the nucleotide sequence of SEQ ID NO:1 or 2; or c) the complement of (a) or (b).

A multiplex PCR as contemplated by the invention may have the general format depicted in FIG. 1. Here, primers P1 and P2 are used for amplifying a segment of the adenoviral hexon gene which is then used as a template for a subsequent amplification reaction by primers P3 and P4. In this format, the primer of SEQ ID NO:3 as primer P1, and the primers of SEQ ID NO:4 and/or SEQ ID NO:5 may be used as primer P2. The subsequent nested PCR can be carried out using the primer of SEQ ID NO:6 (or its longer variant depicted in SEQ ID NO:10) and/or the primer of SEQ ID NO:7 (or its longer variant depicted in SEQ ID NO:11) as forward primer P3. The primer of SEQ ID NO:8 (or its longer variant depicted in SEQ ID NO:12) and/or the primer of SEQ ID NO:9 (or its longer variant depicted in SEQ ID NO:13) will act as reverse primer P4.

The multiplex PCR including the above-described primers may also include primers which are specific for the nucleic acid from one or more other pathogenic microorganisms. Preferably, the multiplex includes primers for the amplification of Influenza virus, such as Influenza virus A and/or Influenza virus B, respiratory syncytial virus, such as subtype A and/or subtype B, parainfluenza virus, such as parainfluenza virus type 1, 2, 3 and/or 4, coronavirus, such as coronavirus NL63, OC43, HKU1, and/or 229E, human metapneumovirus, such as type A and/or B, enterovirus, rhinovirus, bocavirus, and adenovirus, for example, subtypes B and/or E. In multiplex assays for the differential detection of multiple pathogens, the primers and probes of the invention may contain additional sequence portions which serve as binding sites for additional primers, e.g. for universal primers that amplify the amplification products resulting from the gene-specific multiplex primers. For example, the primers depicted in SEQ ID NOs:6-13 may be modified to include at their 5' end a sequence which allows binding of the SuperPrimers used in the ResPlex II Kit. Suitable binding sequences for the SuperPrimers are depicted in SEQ ID NOs:14-17. The SuperPrimers are depicted as P5 and P6 in FIG. 1. The FIGURE also shows a bead-coupled oligonucleotide probe as used in the ResPlex II Kit.

In a further aspect, the invention also relates to the use of an oligonucleotide probe as defined above for the detection of adenoviral nucleic acid, preferably in a PCR, RT-PCR, real-time PCR or real-time RT-PCR reaction. Also included by the scope of the invention is the use of one or more of the oligonucleotide primers defined above for amplifying adenoviral nucleic acid, such as adenoviral DNA or RNA. Preferably, the primers are used in a PCR, RT-PCR, real-time PCR or real-time RT-PCR reaction. In a particularly preferred embodiment of the invention, the primers of the invention can be used in a multiplex PCR, wherein an oligonucleotide comprising: a) the nucleotide sequence of SEQ ID NO:6 or SEQ ID NO:10; or b) a sequence which is at least 85% identical to the nucleotide sequence of SEQ ID NO:6 or SEQ ID NO:10; or c) the complement of (a) or (b) is used as a first forward primer; and an oligonucleotide comprising: a) the nucleotide sequence of SEQ ID NO:7 or SEQ ID NO:11; or b) a sequence which is at least 85% identical to a nucleotide sequence of SEQ ID NO:7 or SEQ ID NO:11; or c) the complement of (a) or (b) is used as a second forward primer; and an oligonucleotide comprising: a) the nucleotide sequence of SEQ ID NO:8 or SEQ ID NO:12; or b) a sequence which is at least 85% identical to a nucleotide sequence of SEQ ID NO:8 or SEQ ID NO:12; or c) the complement of (a) or (b) is used as a first reverse primer; and an oligonucleotide comprising: a) the nucleotide sequence of SEQ ID NO:9 or SEQ ID NO:13; or b) a sequence which is at least 85% identical to a nucleotide sequence of SEQ ID NO:9 or SEQ ID NO:13; or c) the complement of (a) or (b) is used as a second reverse primer.

Finally, the invention also pertains to kit for the detection of adenovirus, comprising at least one oligonucleotide probe of the invention, i.e. at least one oligonucleotide comprising or consisting of the nucleotide sequence of SEQ ID NOs:1 or 2. Kits for amplifying adenovirus nucleic acid, in particular DNA of adenovirus serotypes 1, 2, 3, 4, 5, 6, 7, 11, 14, 16, 21, 34, and 35 are also provided. These kits contain at least one oligonucleotide primer of the invention as defined elsewhere herein. More preferably, the kits include a first oligonucleotide primer comprising: a) the nucleotide sequence of SEQ ID NO:6 or SEQ ID NO:10; or b) a sequence which is at least 85% identical to the nucleotide sequence of SEQ ID NO:6 or SEQ ID NO:10; or c) the complement of (a) or (b); and a second oligonucleotide primer comprising: a) the nucleotide sequence of SEQ ID NO:7 or SEQ ID NO:11; or b) a sequence which is at least 85% identical to a nucleotide sequence of SEQ ID NO:7 or SEQ ID NO:11; or c) the complement of (a) or (b); and a third oligonucleotide primer comprising: a) the nucleotide sequence of SEQ ID NO:8 or SEQ ID NO:12; or b) a sequence which is at least 85% identical to a nucleotide sequence of SEQ ID NO:8 or SEQ ID NO:12; or c) the complement of (a) or (b); and a fourth oligonucleotide primer comprising: a) the nucleotide sequence of SEQ ID NO:9 or SEQ ID NO:13; or b) a sequence which is at least 85% identical to a nucleotide sequence of SEQ ID NO:9 or SEQ ID NO:13; or c) the complement of (a) or (b).

Even more preferably, the kit additionally includes a fifth oligonucleotide primer comprising: a) the nucleotide sequence of SEQ ID NO:3; or b) a sequence which is at least 85% identical to the nucleotide sequence of SEQ ID NO:3; or c) the complement of (a) or (b); and a sixth oligonucleotide primer comprising: a) the nucleotide sequence of SEQ ID NO:4; or b) a sequence which is at least 85% identical to a nucleotide sequence of SEQ ID NO:4; or c) the complement of (a) or (b); and a seventh oligonucleotide primer comprising: a) the nucleotide sequence of SEQ ID NO:5; or b) a sequence which is at least 85% identical to a nucleotide sequence of SEQ ID NO:5; or c) the complement of (a) or (b). The kit may also include one or more oligonucleotide probes comprising or consisting of the nucleotide sequence of SEQ ID NOs:1 or 2.

EXAMPLES

Example 1

Design of a Modified ResPlex II Assay

The present study was conducted on the basis of the ResPlex II Panel v2.0 as available from Qiagen (Hilden, Germany). The ResPlex II Panel v2.0 is a multiplex PCR system which allows for the amplification and detection of gene target from multiple respiratory RNA and DNA viruses in a single assay. The following virus types and subtypes are identified by the ResPlex II Panel v2.0: Influenza A, Influenza B, respiratory syncytial virus subtype A, respiratory syncytial virus subtype B, parainfluenza virus 1, parainfluenza virus 2, parainfluenza virus 3, parainfluenza virus 4, coronavirus NL63, coronavirus OC43, coronavirus HKU1, coronavirus 229E, human metapneumoviruses A and B, enterovirus, rhinovirus, bocavirus, and adenovirus B and E.

For validating the newly developed primers, all primers targeting adenoviral nucleic acid included in the original ResPlex II Panel v2.0 were replaced by the new oligonucleotides. The concentration of the replacement primers was twice as high as that of the original primers. The following oligonucleotide primers were made:

```
ADVuniFo:
                                        (SEQ ID NO: 3)
CAGGACAGAAACACTGA ADVuniRo:
                                        (SEQ ID NO: 4)
GATTAATTTCCAGGGCAAA ADVuni2Ro:
                                        (SEQ ID NO: 5)
TTGGATATTGATTTCCATAGC ADVunitagFi:
                                        (SEQ ID NO: 14)
CAGGCCACGTTTTGTCATGCTTTCTATGTGGAATCAGGC
```

-continued

ADVuni2tagFi:
(SEQ ID NO: 15)
CAGGCCACGTTTTGTCATGCTATGATCCTGATGTICGCATT

ADVunitagRi:
(SEQ ID NO: 16)
TTCTTTGCGTTATGTCTCTGCAGTTCCATGGTTTTCAAT

ADVuni2tagRi:
(SEQ ID NO: 17)
TTCTTTGCGTTATGTCTCTGCACGCCATGATTTTCAAT

The underlined portion of the gene-specific nested primers denotes a sequence which is not complementary to the adenoviral target DNA, but instead serves as a binding site for the universal SuperPrimer as used in the ResPlex II assay system.

The probe used in the original ResPlex II Panel v2.0 for binding to adenoviral DNA was replaced by the following oligonucleotide probe:

(SEQ ID NO: 2)
ADVB_E_DeV_Nis: CGCATTATTGAAAACCATGGC

As a result of the inclusion of the new primers and the new probe, it was expected that the modified ResPlex II Panel exhibits an improved detection range with respect to the different adenovirus serotypes. In particular, it was expected that the new probes and primer result in the detection of adenovirus serotypes from the subtypes C (serotypes 1, 2, 5, and 6) which were not detectable with the original ResPlex II Panel v2.0.

Example 2

Validating the Modified ResPlex II Assay

The functionality of the modified ResPlex II panel was confirmed by using the panel according to the recommendations of the manufacturer regarding the original panel (see ResPlex II Panel v2.0 Handbook, September 2010).

Different adenovirus subtypes relevant for respiratory infections were tested at several concentrations. All samples tested were obtained from the American Type Culture Collection (Rockville, Md., USA). DNA was isolated from the ATCC samples according to common methods. The serotypes used with the modified ResPlex II Panel are set forth in table 1.

TABLE 1

ADV strains tested

| subgroup | serotype |
|---|---|
| ADV B | ADV 3 |
|  | ADV 7a |
|  | ADV 11 |
|  | ADV 14 |
|  | ADV 16 |
|  | ADV 21 |
|  | ADV 34 |
|  | ADV 35 |
| ADV E | ADV 4 |
| ADV C | ADV 1 |
|  | ADV 2 |
|  | ADV 5 |
|  | ADV 6 |

The RT-PCR assay was performed as described in the ResPlex II Panel v2.0 Handbook (September 2010). Briefly, the template RNA, dNTP Mix, amplification enhancer, QIAplex RT-PCR Buffer, ResPlex II Primer Mix, and PCR grade water were thawed and placed on ice as follows:

| | |
|---|---|
| Water (PCR grade): | 19.25 µl |
| 5 x QIAplex RT-PCR Buffer | 10 µl |
| dNTP Mix, 10 nM each | 2 µl |
| ResPlex II Primer Mix | 6 µl |
| QIAgen OneStep RT-PCR Enzyme Mix | 2 µl |
| Amplification Enhancer | 0.75 µl |
| Total volume | 40 µl |

The modified ResPlex II Primer Mix was mixed by vortexing. The master mix was carefully mixed and 40 µl were dispensed into each PCR tube. 10 µl template DNA was given to the individual PCR tubes. In one PCR tube 10 µl water were added instead of DNA as a negative control. In a further tube 10 µl of the ResPlex II v2.0 Positive Control were added instead of template to obtain an amplification check.

The tubes were transferred to a GeneAmp 9700 PCR System (Applied Biosystems) running in 9600 emulation mode. The program run on the thermal cycler was the following:

| | | |
|---|---|---|
| Reverse transcription: | 35 min | 50° C. |
| Initial PCR activation step: | 15 min | 95° C. |
| Enrichment cycling | | |
| Denaturation: | 30 sec | 94° C. |
| Annealing: | 1 min | 52° C. |
| Extension: | 1 min | 72° C. |
| Number of cycles: | 15 | |
| 2-step cycling | | |
| Denaturation: | 15 sec | 94° C. |
| Annealing/extension: | 1.5 min | 70° C. |
| Number of cycles: | 6 | |
| 3-step cycling | | |
| Denaturation: | 15 sec | 94° C. |
| Annealing: | 15 sec | 52° C. |
| Extension: | 15 sec | 72° C. |
| Number of cycles: | 30 | |
| Final extension: | 3 min | 72° C. |

The program includes steps for both reverse transcription and PCR. The PCR amplification segment must start with an initial heating step at 95° C. for 15 min to activate HotStar-Taq DNA Polymerase (Qiagen, catalogue no. 203203). The RT-PCR program was started while the PCR tubes were still on ice. After the thermal cycler had reached a temperature of 50° C., the PCR tubes were placed in the thermal cycler.

After amplification, the amplified viral RNA and DNA sequences were detected. In a first step, QIAplex stopping buffer was heated to 52° C. and kept at that temperature until use. The modified ResPlex II bead mix containing beads coupled to the oligonucleotide probe with the sequence of SEQ ID NO:2 was mixed by vortexing. Both the bead mix and the reaction mix were protected from light by covering the tubes and the microtiter plate with foil.

A detection mix was prepared consisting of 35 µl detection buffer and 10 µl modified ResPlex II bead mix. The detection mix contains all the components needed for the reaction except the PCR products and the diluted QIAplex SA-PE. The reaction mix was vortexed, and 45 µl were dispensed into each well of a 96-well, flat-bottom plate. For each assay, 5 μl of the RT-PCR reaction are added to a sample well. The samples were incubated at 52° C. in the dark for 10 min.

A fresh 1:1 mixture of detection buffer:QIAplex SA-PE was prepared at room temperature. 10 μl of the mixture were used per assay. The mixture was kept in a dark place to protect from light until use. 10 μl of the mixture of detection buffer:QIAplex SA-PE were given to each sample. The samples were kept at 52° C., and mixed briefly by pipetting up and down. The samples were incubated at 52° C. in the dark for 5 min. 120 μl QIAplex Stopping Buffer prewarmed to 52° C. were added to each reaction. All samples were kept at 52° C. and protected from light until analysis. The samples were analyzed on a LiquiChip200 Workstation (Qiagen, Hilden, Germany) using QIAplex MDD Software according to the instructions of the manufacturer.

As a result, it was found that all of the tested adenovirus serotypes (1-5 and 7a) were detected by the modified ResPlex II Panel. Evidently, there was no interference of the novel probe and primers with other primers or probes in the panel. Therefore, the new probes and primers make a significant contribution, because they increase the number of viruses that can be detected with the ResPlex II Panel.

Example 3

Sensitivity of the Modified ResPlex II Assay

To evaluate the specificity and sensitivity of the modified ResPlex II Panel, a direct comparison of the modified assay with the CE ("Communauté Européenne") marked xTAG Respiratory Viral Panel (RVP) assay was performed. The xTAG Respiratory Viral Panel is a qualitative nucleic acid multiplex test for the simultaneous detection of multiple respiratory virus nucleic acids in nasopharyngeal swabs, nasal aspirates, and bronchoalveolar lavages from subjects suspected of respiratory tract infections.

The following virus types and subtypes are identified using RVP: Influenza A, Influenza A subtype H1, Influenza A subtype H3, Influenza A subtype H5, Influenza B, respiratory syncytial virus subtype A, respiratory syncytial virus subtype B, parainfluenza viruses 1-4, coronavirus NL63, coronavirus OC43, coronavirus HKU1, coronavirus 229E, coronavirus SARS, human metapneumovirus, enterovirus, rhinovirus, and adenovirus serotypes B, C and E.

Virus material obtained from the American Type Culture Collection from different adenoviral subtypes was tested. Nucleic acid extraction was done using the QIAcube (Qiagen, Hilden, Germany) following the protocol described in the official manual. Resulting eluates were tested in serial dilutions using the ResPlex II Advanced Panel and the xTAG RVP test. The results of this analysis are summarized in table 2.

TABLE 2

ADV detection using ResPlex II Panel and xTAG RVP:

| | ATCC samples | ResPlex II Advanced | |
|---|---|---|---|
| serotype | dilution | PRE-Version | xTAG RVP |
| ADVB7a | LoD 4 | 748 | 178 |
| ADVB3 | 1:50.000 | 2621 | 961 |
| ADVB3 | 1:500.000 | 1206 | 273 |
| ADVB3 | 1:5.000.000 | 160 | |
| ADVB3 | 1:50.000.000 | 38 | |
| ADVE4 | LoD 2 | 353 | 80 |
| ADVC1 | 1:2.500 | 3578 | 1720 |
| ADVC1 | 1:25.000 | 1859 | 1158 |
| ADVC1 | 1:250.000 | 272 | 686 |
| ADVC1 | 1:2.500.000 | 29 | 75 |
| ADVC2 | 1:20.000 | 3116 | 1350 |
| ADVC2 | 1:200.000 | 1504 | 285 |
| ADVC2 | 1:2.000.000 | 83 | 57 |
| ADVC2 | 1:20.000.000 | 19 | 53 |
| ADVC5 | 1:500.000 | 5676 | 1248 |
| ADVC5 | 1:5.000.000 | 3847 | 481 |
| ADVC5 | 1:50.000.000 | 899 | 192 |
| ADVC5 | 1:500.000.000 | 114 | 62 |

All data generated are presented in MFI=Mean Fluorescence Intensities. For the modified ResPlex II assay, all signals above 250 MFI are designated as positive (cutoff=250 MFI). For the xTAG assay all signals above 300 MFI are designated as positive (cutoff=300 MFI). Consequently, all samples detected as positive result for any of the test methods used were highlighted in bold.

The results clearly show that the modified ResPlex II assay provides higher sensitivity and specificity with regard to detection of different adenovirus serotypes compared to the xTAG RVP assay. Serotypes 7a and 4 were successfully detected with the modified ResPlex II, but no signal was generated using xTAG RVP. For serotypes 3, 2 and 5 higher sensitivity (1 log each) of the modified ResPlex II assay was achieved. For ADV 1, a comparable sensitivity was achieved. Taken together the novel probe and the novel primers implemented in the modified ResPlex II Panel provides reliable detection of different adenovirus subtypes including higher sensitivity and specificity than the CE marked and FDA (Food and Drug Administration) approved xTAG RVP kit.

The invention claimed is:

1. A method for detecting adenoviral nucleic acid from an adenovirus that causes respiratory infections in a biological sample, comprising:
   a) obtaining viral nucleic acid from a biological sample that is suspected to include material from an adenovirus that causes respiratory infections;
   b) amplifying the viral nucleic acid;
   c) contacting an oligonucleotide probe with the amplified viral nucleic acid obtained in step b), said probe comprising:
      i) the nucleotide sequence of SEQ ID NO:1 or SEQ ID NO:2; or
      ii) a sequence which is at least 85% identical to the nucleotide sequence of SEQ ID NO:1 or SEQ ID NO:2; or
      iii) the full complement of (i) or (ii), wherein said probe comprises a detectable moiety and wherein said probe is a universal probe that hybridizes specifically to adenovirus serotypes that causes respiratory infections in humans; and
   d) detecting specific hybridization of the oligonucleotide probe to the amplified viral nucleic acid;
   wherein the specific hybridization of said oligonucleotide probe in step c) i) indicates that the biological sample contains adenovirus nucleic acid from an adenovirus that causes respiratory infections, and wherein no hybridization of said oligonucleotide probe in step c) i) indicates that the biological sample does not contain nucleic acid from an adenovirus that causes respiratory infections.

2. The method according to claim 1, wherein said oligonucleotide probe comprises:
   a) the nucleotide sequence of SEQ ID NO:2; or
   b) a sequence which is at least 85% identical to the nucleotide sequence of SEQ ID NO:2; or
   c) the full complement of (a) or (b).

3. The method according to claim 1, wherein said oligonucleotide probe consists of the sequence of SEQ ID NO:1 or SEQ ID NO:2.

4. The method according to claim 1, wherein the oligonucleotide probe is linked to a bead.

5. The method according to claim 4, wherein said bead is a colour-coded bead.

6. The method according to claim 1, wherein said biological sample is derived from a human.

7. The method according to claim 1, wherein the biological sample is a biopsy, blood, serum, plasma, urine, stool, sputum, bronchial lavage, or liquor sample or a nasal or throat swab.

8. The method according to any of claim 1, wherein the adenovirus nucleic acid to be detected is adenovirus DNA.

9. The method according to claim 8, wherein the adenovirus DNA is from the adenoviral hexon gene.

10. The method according to claim 1, wherein the amplification in step b) is effected using one or more oligonucleotide primers comprising:
   a) the nucleotide sequence of any of SEQ ID NOS:3-9; or
   b) a sequence which is at least 85% identical to a nucleotide sequence of any of SEQ ID NOS:3-9; or
   c) the complement of (a) or (b).

11. The method according to claim 1, wherein the amplification in step b) is effected using one or more oligonucleotide primers comprising:
   a) the nucleotide sequence of any of SEQ ID NOS:10-13; or
   b) a sequence which is at least 85% identical to a nucleotide sequence of any of SEQ ID NOS:3-5 and 10-13; or
   c) the complement of (a) or (b).

12. The method according to claim 1, wherein the amplification in step b) is effected using one or more oligonucleotide primers consisting of a nucleotide sequence of any of SEQ ID NOS:3-13.

13. The method according to claim 1, wherein amplification in_step b) is effected using a multiplex PCR.

14. The method according to claim 13, wherein the multiplex PCR is effected using:
   (i) as a first forward primer an oligonucleotide comprising:
      a) the nucleotide sequence of SEQ ID NO:6 or SEQ ID NO:10; or
      b) a sequence which is at least 85% identical to the nucleotide sequence of SEQ ID NO:6 or SEQ ID NO:10; or
      c) the full complement of (a) or (b);
   (ii) as a second forward primer an oligonucleotide comprising:
      a) the nucleotide sequence of SEQ ID NO:7 or SEQ ID NO:11; or
      b) a sequence which is at least 85% identical to a nucleotide sequence of SEQ ID NO:7 or SEQ ID NO:11; or
      c) the full complement of (a) or (b);
   (iii) as a first reverse primer an oligonucleotide comprising:
      a) the nucleotide sequence of SEQ ID NO:8 or SEQ ID NO:12; or
      b) a sequence which is at least 85% identical to a nucleotide sequence of SEQ ID NO:8 or SEQ ID NO:12; or
      c) the full complement of (a) or (b); and
   (iv) as a second reverse primer an oligonucleotide comprising:
      a) the nucleotide sequence of SEQ ID NO:9 or SEQ ID NO:13; or
      b) a sequence which is at least 85% identical to a nucleotide sequence of SEQ ID NO:9 or SEQ ID NO:13; or
      c) the full complement of (a) or (b).

15. The method according to claim 14, wherein the multiplex PCR further uses
   (i) as a third forward primer an oligonucleotide comprising:
      a) the nucleotide sequence of SEQ ID NO:3; or
      b) a sequence which is at least 85% identical to the nucleotide sequence of SEQ ID NO:3; or
      c) the full complement of (a) or (b); and
   (ii) as a third reverse primer an oligonucleotide comprising:
      a) the nucleotide sequence of SEQ ID NO:4 or SEQ ID NO:5; or
      b) a sequence which is at least 85% identical to a nucleotide sequence of SEQ ID NO:4 or SEQ ID NO:5; or
      c) the full complement of (a) or (b).

* * * * *